(12) United States Patent
Beyer et al.

(10) Patent No.: US 10,119,906 B2
(45) Date of Patent: *Nov. 6, 2018

(54) METHOD OF DETERMINING THE CONCENTRATION OF A GAS COMPONENT AND A SPECTROMETER FOR THIS PURPOSE

(71) Applicant: SICK AG, Waldkirch (DE)

(72) Inventors: Thomas Beyer, Waldkirch (DE); Julian Edler, Waldkirch (DE)

(73) Assignee: SICK AG, Waldkirch (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/192,120

(22) Filed: Jun. 24, 2016

(65) Prior Publication Data
US 2016/0377536 A1 Dec. 29, 2016

(30) Foreign Application Priority Data

Jun. 29, 2015 (EP) .................................... 15174243

(51) Int. Cl.
*G01N 21/39* (2006.01)
*G01J 3/42* (2006.01)
(Continued)

(52) U.S. Cl.
CPC ........ *G01N 21/39* (2013.01); *G01J 2003/423* (2013.01); *G01J 2003/4332* (2013.01);
(Continued)

(58) Field of Classification Search
CPC ............. G01N 21/39; G01N 2021/399; G01N 2201/0691; G01N 33/0062; G01N 21/031; G01J 2003/423; G01J 2003/4332
See application file for complete search history.

(56) References Cited

U.S. PATENT DOCUMENTS 7,616,316 B1  11/2009  Silver et al.
8,994,947 B2 *  3/2015  Patel ...................... G01N 21/39
                                              356/432

(Continued)

FOREIGN PATENT DOCUMENTS

DE         10238356 A1    1/2004
DE      102012223874 B3    5/2014
KR      1020090107729 A   10/2009

OTHER PUBLICATIONS

Kraetschmer, et al. "Background-free Absorption Spectroscopy Using Delayed Balanced Detection"; Applied Physics B; Rapid Communication; Published online Dec. 11, 2009.

(Continued)

*Primary Examiner* — Sang H Nguyen
(74) *Attorney, Agent, or Firm* — Nath, Goldberg & Meyer; Jerald L. Meyer

(57) ABSTRACT

The invention relates to a method of determining the concentration of a gas component comprising the steps:
 generating and guiding a light beam having a wavelength variable in a wavelength range through a measurement volume in which the gas component having an absorption in the wavelength range is present;
 tuning the wavelength range;
 detecting the intensity of the light beam after passage through the measurement volume;
 storage of measurement points during the tuning that respectively consist of a point in time and an associated intensity value, to obtain a direct absorption line;
 generating an artificial measurement curve from the stored measurement points by shifting the measurement points on the time axis;
 wherein the shift takes place so that an artificial modulation results in the wavelength time extent; and
 evaluating the artificial measurement curve in accordance with the method of the wavelength modulation spectroscopy and determining a first concentration value therefrom.

15 Claims, 4 Drawing Sheets

Figure 1:
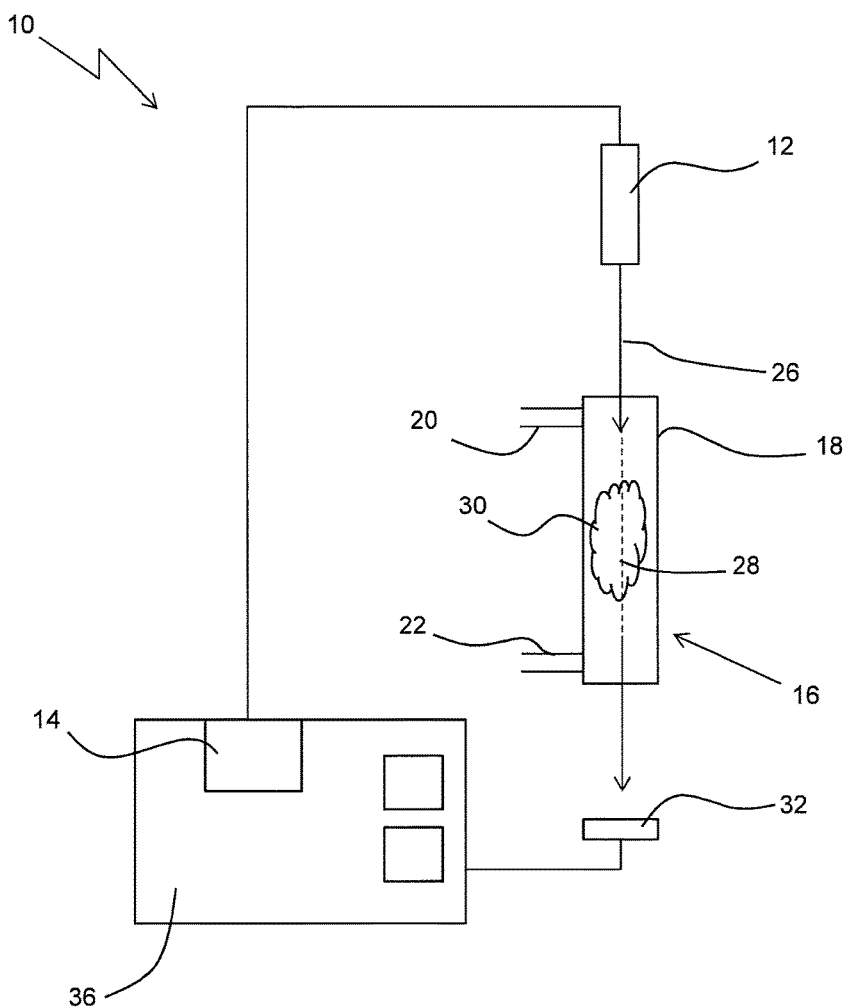

(51) Int. Cl.
  *G01J 3/433* (2006.01)
  *G01N 33/00* (2006.01)
  *G01N 21/03* (2006.01)

(52) U.S. Cl.
  CPC ....... *G01N 21/031* (2013.01); *G01N 33/0062* (2013.01); *G01N 2021/399* (2013.01); *G01N 2201/0691* (2013.01)

(56) References Cited

U.S. PATENT DOCUMENTS

| | | | | |
|---|---|---|---|---|
| 2006/0044562 | A1* | 3/2006 | Hagene | G01N 21/39 356/437 |
| 2007/0295908 | A1* | 12/2007 | Wilkins | G01N 21/274 250/339.09 |
| 2009/0059234 | A1* | 3/2009 | Dreyer | G01J 3/02 356/437 |
| 2012/0283961 | A1* | 11/2012 | Wittmann | G01N 21/39 702/24 |
| 2014/0204382 | A1* | 7/2014 | Christensen | G01N 21/39 356/402 |
| 2014/0299774 | A1* | 10/2014 | Kaufmann | G01J 3/108 250/339.07 |
| 2014/0340684 | A1* | 11/2014 | Edler | G01J 3/4338 356/409 |
| 2015/0085288 | A1* | 3/2015 | Steinbacher | G01N 21/39 356/437 |
| 2015/0338342 | A1* | 11/2015 | Muramatsu | G01N 21/39 356/409 |

OTHER PUBLICATIONS

European Search Report dated Dec. 23, 2015 corresponding to application No. 15174243.4-1554.

* cited by examiner

METHOD OF DETERMINING THE CONCENTRATION OF A GAS COMPONENT AND A SPECTROMETER FOR THIS PURPOSE

The invention relates to a method of determining the concentration of a gas component and to a spectrometer for carrying out the method.

For determining the concentration of a gas component of a measurement gas, different methods are known. These include the direct absorption spectroscopy (DAS) and the wavelength modulation spectroscopy (WMS).

In the direct absorption spectroscopy, the wavelength of a laser is varied via a current ramp and the detector signal is recorded. Light is absorbed by the measurement gas in accordance with Lambert-Beer's law on tuning the current ramp when the laser passes through the range of the absorption line.

$$I = I_0 * e^{-\alpha(\lambda)cL}$$

where $\alpha(\lambda)$ is a wavelength dependent absorption,
c is the gas concentration,
and L is the path via which the gas is absorbed.

The detector signal is deformed thereby in such a way that an absorption line can be recognized in comparison to a detector signal without a gas absorption that is then fitted e.g. by a fit having a physical model function (generally a Voigt absorption line) and in this way the absorption surface (area under the absorption curve) that is proportional to the gas concentration can be determined.

The wavelength modulation spectroscopy (WMS) is a form of optical absorption spectroscopy that enables a detection of very small optical absorptions, as the absorption measurements of small frequencies (close to DC) in which the light source has large noise is displaced to high frequencies in which the shot-noise is the limiting factor. This frequency shift can improve the measurement sensitivity by three to five orders of magnitude.

The WMS is generally carried out with continuously tunable lasers, such as diode lasers (TDL). In this respect the wavelength is slowly tuned across an absorption line of the measurement gas and is additionally modulated slightly with a high modulation frequency f with respect thereto, typically in a sinusoidal manner. When the light beam wavelength modulated in this way propagates through the measurement path an amplitude modulation of the light results from the intensity change of the laser and through the absorption of the measurement gas. When the light is then detected in the light receiver and a received signal is generated in dependence on time, then the received signal includes AC components for the modulation frequency f and its harmonics 2f, 3f, 4f etc. One of the AC components can be selected for the evaluation and can be evaluated in a phase sensitive method e.g. with a lock-in method. This method is also referred to as demodulation. The signal received on a demodulation at the frequency nf is referred to as nf signal (n=1, 2, 3, . . . ). The demodulated signal in this way includes pieces of information with respect to the optical absorption and with respect to the intensity of the light beam. Via the so measured absorption, concentrations of a gas component of the measurement gas to be investigated can be determined.

A detailed theory that describes the WMS and the relationship between the shape of the absorption line and the shape of the demodulated signal is given in "Frequency-modulation spectroscopy for trace species detection: theory and comparison among experimental methods", Applied Optics 31, 707-717 (1992). The signal shape that is obtained on the WMS, when one slowly tunes over the absorption line and simultaneously modulates the wavelength at the frequency of qualitatively corresponds to the n-th derivative of the absorption line which is why the description derivative absorption spectroscopy is also used for the WMS.

From the DE 102 38 356 A1 a method is known in which the two measurement methods WMS and DAS are used alternatively in periods following one another and the detected signals are likewise supplied alternatively to two separate mean value formations for the purpose of evaluation. Having regard to the WMS evaluation, the results of the DAS evaluation can be drawn on, e.g. for calibration. In this way one obtains the calibration freedom of the direct absorption spectroscopy and the accuracy of the wavelength modulation spectroscopy.

Having regard to a method known from the U.S. Pat. No. 7,616,316 B2, a switch is made between the DAS at high concentrations of the gas component to be measured and WMS at low concentrations of the gas to be measured. Thus, the measurement method that appears to be most suitable is used.

From the DE 10 201 2 223 874 B3 both measurement methods WMS and DAS are used simultaneously or as in the DE 102 38 356 A1 alternatively and the two measurement results are linked by mean value formation, whereby smaller errors in the result can be achieved.

The invention has the aim of increasing the functional safety (SIL; Safety-Integrated-Level) having regard to the gas concentration determinations in order to be able to satisfy safety norms that define the SIL. In the functional safety it can be that an error tolerance of 1 is required. This normally relates to the hardware. Independent of the used hardware non-random errors can, however, arise on the measurement of the gas concentration due to external influences, such as intensity fluctuations, pressure changes, pressure, temperature and interferences. For this reason it is an object of the invention to make available a method and a spectrometer for determining a gas component which are respectively improved with respect to the functional safety.

Such an increase of the safety can be achieved on the application of two different measurement methods, DAS and WMS, as are known from the DE 102 38 356 A1 and the DE 10 2012 223 874 B3 respectively. However, it is disadvantageous that a doubling of the demand in effort and cost with respect to time and apparatus is brought about. Having regard to the simultaneous application of the measurement method disclosed in the DE 10 2012 223 874 B3 the laser has to be controlled with a ramp, plus a sinusoidal modulation. This is disadvantageous for the DAS, since the direct detector signal having regard to the WMS is not suitable for an evaluation according to the DAS, as the sinusoidal modulation does not only lead to a performance modulation, but also to a wavelength modulation. Also following an averaging over e.g. a sinusoidal period, the absorption is slurred by the sinusoidal modulation and the evaluation becomes difficult and can no longer be achieved via a fit with a physical model. The result of such a DAS is thus not as conclusive as the laser is controlled in a non-favorable manner for this purpose.

For this reason the invention solves the problem in a different way and indeed by a method in accordance with claim 1 and respectively by a spectrometer in accordance with claim 10.

The method in accordance with the invention for determining the concentration of a gas component comprises the following steps:

generating a light beam having a wavelength variable in a wavelength range;

guiding the light beam through a measurement volume in which the gas component to be determined is present, with the gas component having an absorption in the wavelength range;

tuning the wavelength range;

detecting the intensity of the light beam after a passage through the measurement volume;

storage of measurement points during the tuning that respectively consist of a point in time and an associated intensity value, whereby a direct absorption line is obtained;

generating an artificial measurement curve from the stored measurement points by shifting the measurement points on the axis of time;

wherein the shift takes place in such a way that an artificial modulation results in the wavelength time extent following the shift of the measurement points; and evaluating the artificial measurement curve in accordance with the methods of measurement wavelength modulation spectroscopy and determining a first concentration value therefrom.

The central idea is thus the carrying out of only one measurement and indeed by a control of the laser, this means by a tuning of the wavelength range, i.e. by changing (sweeping through) the respective wavelengths of the wavelength range, for a measurement in accordance with the DAS. The obtained measurement signals are, however, then evaluated in accordance with the two methods of the DAS and respectively of the WMS. In this way two results are obtained by way of two different paths. This is only possible through the storage of the measurement points and through a new stringing together (shift) of the measurement points for the generation of an artificial measurement curve, that is composed of the current measurement values and that can then be evaluated in accordance with the WMS. This is where the essential idea lies.

The essential advantage of such a method is that the evaluation of a detector signal with two different evaluation methods is possible such that external influences cannot generate non-random errors, whereby a high SIL level can be achieved.

A further advantage is that the "high frequency behavior" of the laser with respect to WMS, this means changes of the laser that only occur due to the fast sinusoidal modulation of the laser current in the laser wavelength, no longer play a role. Such changes result from the fact that the change in wavelength is initiated in particular by thermal effects and these normally take place slowly and cannot follow the fast sinusoidal modulation in such a way that the wavelength modulation inadvertently becomes smaller and only the intensity modulation remains. These changes of the laser properties no longer play a role in the method in accordance with the invention, as the measurement curve for the WMS evaluation was merely established by resorting (shifting) of the measurement points on the axis of time and the measurement points were obtained without the fast sinusoidal modulation.

A further advantage is that the complete measurement is very fast as only the adjustment of the laser along the ramp (tuning through the wavelength range) is required and none of the components have to longer follow a fast sinusoidal modulation. Higher repetition rates of the ramp (tuning) are thus possible, as the modulation generated retroactively by a resorting of the measurement points is independent of the frequency response of the amplifier for the detector signal and no sinusoidal modulation has to be recorded.

In order to achieve a certain SIL level it is sensible to obtain a second concentration value, which in an embodiment of the invention takes place thereby that, following the storage of the measurement points, an evaluation of the direct absorption line is carried out in accordance with the method of the direct absorption spectroscopy and a second concentration value is determined.

In this way the two generated concentration values can be used for the purpose of achieving a higher level with respect to the functional safety by a plausibilization of the values.

The two concentration values obtained on the different paths can be compared to one another in order to merely use one of these two values for a verification of the other one.

Additionally or alternatively a common concentration value can be generated from the two concentration values by mean value formation, the common concentration value then having a smaller error than the individual value.

It is sensible and reduces the demand in effort and cost when the tuning of the wavelength range takes place without additional high frequency modulation of the wavelength during the tuning in such a way that a monotonous wavelength time extent results without high frequency modulation.

In different embodiments of the invention the artificial modulation can be adapted to a desired WMS evaluation. Such an adaptation can relate to the modulation itself that can typically be sinusoidal, but also rectangular or triangular. Also the amplitude and/or the frequency of the modulation can be adapted by a corresponding shift of the measurement points for the evaluation in accordance with the wavelength modulation spectroscopy. Likewise the phase of the artificial modulation can be adapted in such a way that on the evaluation in accordance with the wavelength modulation spectroscopy the result is only present in the real part of the Fourier transform.

Such adaptations of the artificial modulation that can be brought about in a very simple manner, as the measurement points only have to be correspondingly shifted for this purpose, this means that they can be strung together differently and newly, means that the evaluation can be simplified or improved in a desirable way.

A spectrometer in accordance with the invention by means of which the method can be carried out comprises:

a light source for generating a light beam having a wavelength variable in a wavelength range, a measurement volume in which the gas component to be determined is present and through which the light beam propagates;

control means for the light source for tuning the wavelength range without additional high frequency modulation of the wavelength during the tuning such that a monotonous wavelength time extent results without high frequency modulation;

a light detector for detecting the intensity of the light beam after passage through the measurement volume;

storage means for the storage of measurement points that respectively consist of a point in time and an associated intensity value during the tuning, whereby a direct absorption line is obtained;

an evaluation unit for generating an artificial measurement curve from the stored measurement points by shifting the measurement points on the axis of time, wherein the shift takes place in such a way that an additional high frequency modulation results in the wavelength time extent following the displacement and in this way a new stringing together results in the wavelength time extent;

and for evaluating the artificial measurement curve in accordance with the methods of the wavelength modulation spectroscopy and determining a first concentration value therefrom.

Advantageously the evaluation unit is configured in such a way that the measurement points that respectively consist of a point in time and the associated intensity value are evaluated in accordance with the method of the direct absorption spectroscopy and in this way a second concentration value can be determined.

In an embodiment, the light source is a tunable laser whose emission wavelength can be changed by a control current or a control voltage.

In an embodiment of the invention the tuning takes place through a linear change of the control current or of the control voltage. A linear change is simple to produce and also permits a relatively simple resorting (shift) of the stored measurement points in order to introduce the additional modulation.

Alternatively the tuning could also take place by a non-linear change of the control current. Thus, one could for example control the laser with an arbitrary pulse shape which would significantly simplify the control; however, possibly at the expense of a larger demand in effort and cost having regard to the resorting of the measurement points in order to achieve the additional modulation.

Figure 2:
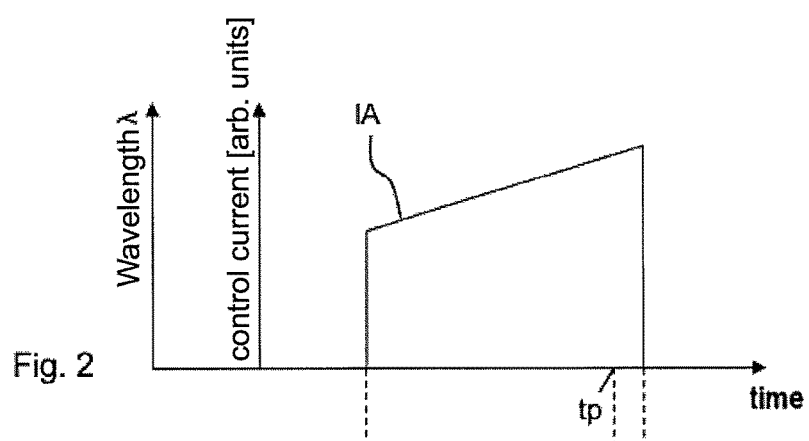
Figure 3:
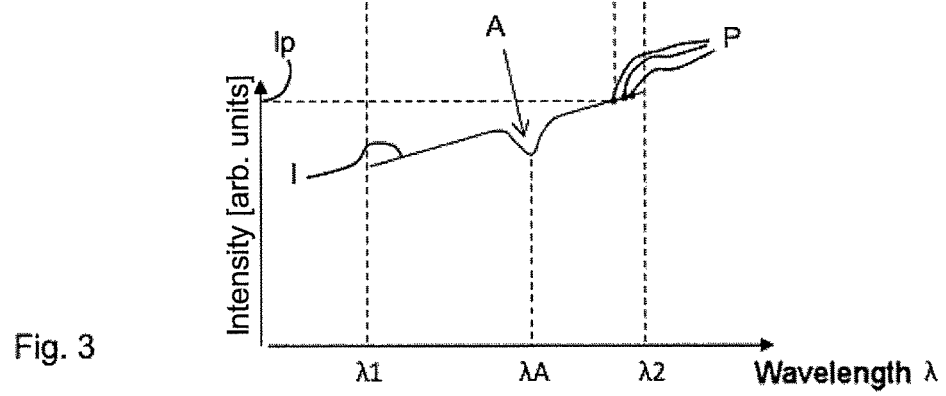
Figure 4:
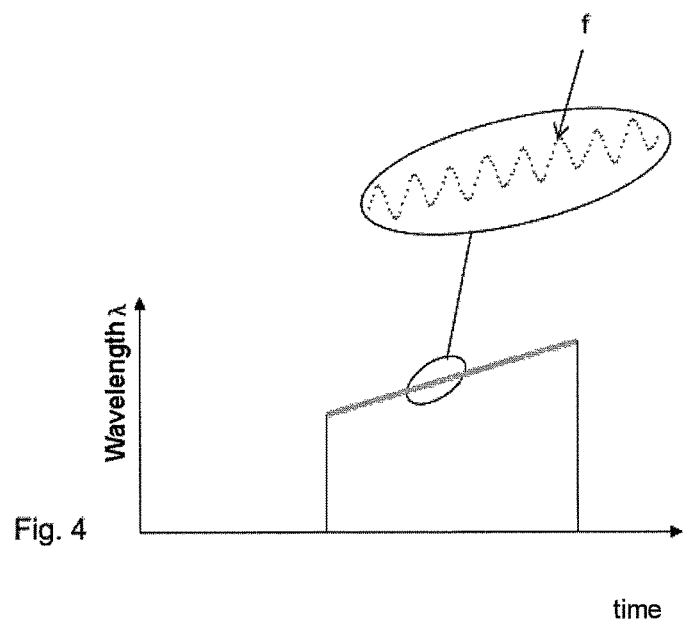
Figure 5:
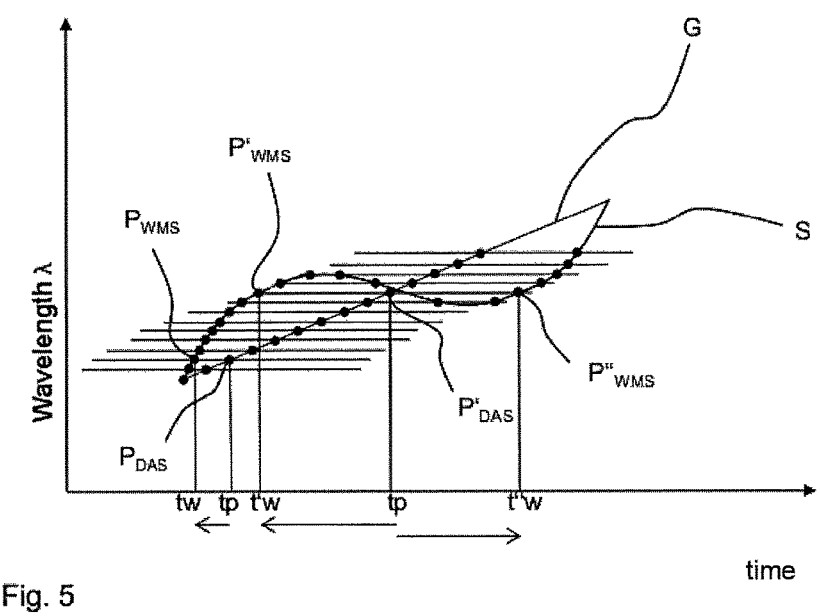
Figure 6:
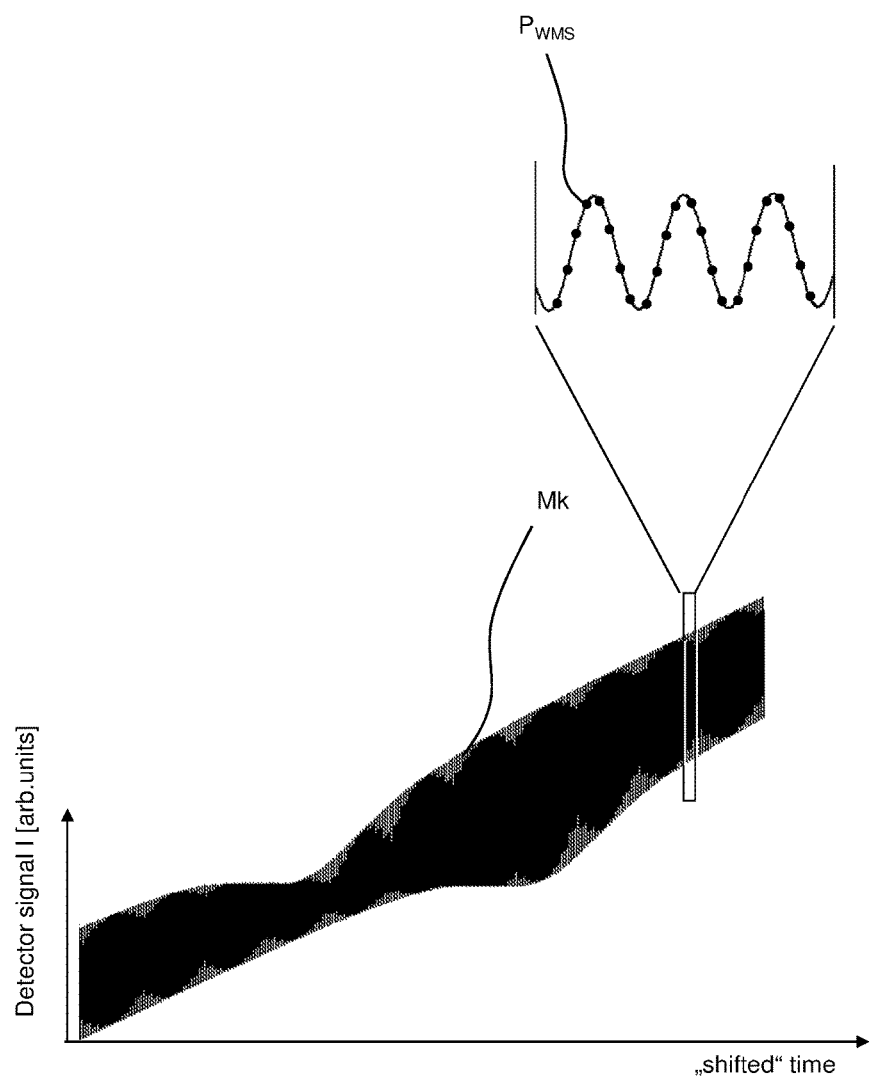

In the following the invention will be described by means of an embodiment with reference to the drawing in detail. In the drawing there is shown:

FIG. 1 a schematic illustration of the spectrometer in accordance with the invention;

FIG. 2 a qualitative, schematic illustration of the laser control;

FIG. 3 a qualitative, schematic illustration of an absorption signal of a measurement gas component;

FIG. 4 an illustration like FIG. 2 after shifting the points on the scale in time;

FIG. 5 an illustration of an extract of FIG. 4 for clarifying the shifting of the points on the scale in time; and FIG. 6 an illustration of the artificial measurement curve after shifting the points at the time scale.

A spectrometer 10 in accordance with the invention schematically illustrated in FIG. 1 has a light source 12 that is preferably configured as a tunable diode laser (TDL), that can be controlled with control means 14. The tunable range corresponds to a wavelength range [$\lambda 1$, $\lambda 2$]. For tuning, a control current IA is provided at the diode laser 12 by means of the control means 14 in such a way that a corresponding wavelength $\lambda$ is generated in dependence on the current intensity. In FIG. 2 the current intensity IA of the control current is applied in dependence on the time t. When the current intensity IA changes this also changes the wavelength $\lambda$ shown as should be indicated by the two ordinate axes in FIG. 2 and the comparison of FIG. 2 and FIG. 3.

Furthermore, the spectrometer 10 has a measurement volume 16 that can be formed from a measurement cell 18 having a measurement gas inlet 20 and a measurement gas outlet 22. Other arrangements e.g. open systems ("open path") or a tube line ("cross duct") that conducts the measurement gas connected thereto are plausible. A measurement gas 30 having a gas component whose concentration shall be measured is present in the measurement cell 18.

The light of the laser 12 is coupled into the measurement cell 18. The optical path within the measurement cell forms an optical measurement part 28. The optical path can be extended via one or more reflectors within or outside of the measurement cell, for example in the shape of a white cell or Herriott cell in order to thus obtain a longer optical measurement path 28.

The measurement gas 30 that has the gas component to be measured is present in the measurement cell 18. The gas component has an absorption A in the tunable wavelength range in such a way that the measurement path 28 absorbs light of the laser 12 propagating along the measurement path 28 at the absorption wavelength $\lambda A$. This is illustrated in FIG. 3 that shows the light intensity I transmitted through the measurement cell 18 in dependence on the wavelength $\lambda$.

Furthermore, a light detector 32 is provided that adapts the light that has propagated along the measurement path. The detector 32 can be a photodiode, an avalanche photodiode or a photo multiplier (PM). The light detector 32 generates a received signal in dependence on the intensity of the incoming light.

The one electrical received signal then includes all pieces of information. It is optionally amplified and/or filtered and supplied to the evaluation unit 36. From a received signal finally the concentrations of the gas components are determined in the evaluation unit 36.

The significance of the individual components and their particular designs and functions will become evident in the subsequent description when the functional principle of the spectrometer 10 in accordance with the invention is described. In this connection it is assumed that the functional principle of the DAS and the WMS as they were also initially explained, are known in principle.

In accordance with the invention the tunable laser 12 is controlled by means of the control means 36. The control generally takes place via the control current IA having regard to diode lasers. The laser emits a certain wavelength $\lambda$ in accordance with the control current IA. The laser 12 controlled in this way covers the wavelength range [$\lambda 1$, $\lambda 2$] (FIGS. 2 and 3).

The control of the laser 12 takes place with a current ramp, such as it is shown in FIG. 2. In this example the current ramp is linear, this means that the control current IA changes linearly with respect to time. For the measurement, the current ramp is repeatedly adjusted with a repetition rate and in this way the measurement is repeated at the repetition frequency.

During the tuning of the wavelength range measurement points P are recorded that together form the intensity extent I and of which only three are illustrated by way of example in FIG. 3. Each measurement point P consists of a point in time tp and an associated intensity value Ip.

The intensity extent I shows the direct absorption line A at the absorption wavelength $\lambda A$. The direct absorption line A is evaluated in the evaluation unit 36 in accordance with the methods of the direct absorption spectroscopy and provides a second concentration value.

In a next step the stored measurement points P of a tuning are now taken and from these a new artificial intensity extent is generated, this means an artificial measurement curve is generated. In this respect one proceeds as follows. And indeed the measurement points P are shifted on the axis in time (abscissa) and are quasi newly strung together or expressed differently are "resorted". In this respect the shift takes place in such a way that in a wavelength time diagram resulting after the shift (new stringing together) as is illustrated in FIG. 4 an additional high frequency modulation f having a small amplitude would show and not a linear extent as is shown in FIG. 2. The small amplitude and high frequency can be recognized in FIG. 4 only in an enlarged section.

The shift (resorting or respectively the newly stringing together) should be explained with reference to FIG. 5. There only a small section is illustrated from the wavelength time diagram of the FIG. 4. The points $P_{DAS}$ and/or $P'_{DAS}$ drawn in FIG. 4 are bijectively associated via the points in time tp with respect to the stored measurement points P. Each point $P_{DAS}$, $P'_{DAS}$ has a coordinate in time tp and a wavelength coordinate. Having regard to a linear tuning the points $P_{DAS}$ and/or $P'_{DAS}$ lie on a straight line G as is shown in FIG. 5.

However, the shift now takes place (new stringing together) and indeed in such a way that the sinusoidal extent S now results on the straight line G modulated thereon. For this purpose it requires a shift of the point $P_{DAS}$ on the axis in time (horizontal) to a new point in time tw so that the point $P_{DAS}$ is displaced to $P_{WMS}$. This takes place in an analog manner for the other points. In order to obtain a clean sinusoidal extent some of the points $P_{DAS}$ have to be shifted a plurality of times to different new points in time. Thus, for example the time $P'_{DAS}$ has to be shifted from its point in time tp, on the one hand, to t'w and, on the other hand to t"w. The point $P'_{DAS}$ has thus quasi been doubled and following the new stringing together appears twice. Depending on the frequency and the amplitude of the sinusoidal extent S to be achieved and the inclination of the straight line G it can also occur that measurement points $P_{DAS}$ are shifted more than twice.

By way of the thus shifted and newly strung together measurement points P that each also have an intensity value, an artificial measurement curve Mk is now constructed in the evaluation unit, such as it is illustrated in FIG. 6. The measurement curve Mk of the FIG. 6 is composed of a plurality of individual measurement points $P_{WMS}$ that are generated by a shift on the axis in time corresponding to the previously mentioned explanations and which, due to the high frequency of the modulation, are not individually recognizable, but only in such an illustration that illustrates the total tunable range (in this way one can see the absorption) and only appear as a "black mass".

The artificial absorption curve Mk is now evaluated in the evaluation unit 36 in accordance with the methods of the wavelength modulation spectroscopy and therefrom a first concentration value is determined.

The invention claimed is:

1. A method of determining the concentration of a gas component, the method comprising the steps of:
   generating a light beam with a light source, the light beam having a wavelength variable in a wavelength range;
   guiding the light beam through a measurement volume in which the gas component to be determined is present, wherein the gas component has an absorption in the wavelength range;
   tuning the wavelength range with a light source controller;
   detecting an intensity of the light beam with a light detector after passage of the light beam through the measurement volume;
   storing measurement points in memory, the measurement points respectively consisting of a point in time and the associated intensity value during the tuning, whereby a direct absorption line is obtained;
   generating an artificial measurement curve from the stored measurement points with an evaluation unit, the evaluation unit shifting the measurement points on the axis of time to generate the artificial measurement curve, wherein the shift takes place such that an artificial modulation of the wavelength results following the shift in the wavelength time extent; and
   evaluating the artificial measurement curve, with the evaluation unit, in accordance with the methods of wavelength modulation spectroscopy and determining a first concentration value therefrom.

2. The method in accordance with claim 1, in which an evaluation of the direct absorption line is carried out in accordance with the method of the direct absorption spectroscopy and a second concentration value is determined following the storage of the measurement points.

3. The method in accordance with claim 2, in which the two generated concentration values are used for the purpose of achieving an increased safety with respect to a functional safety by a plausibilization of the values with respect to one another.

4. The method in accordance with claim 2, in which a common concentration value is generated from the two concentration values.

5. The method in accordance with claim 1, in which the tuning of the wavelength range takes place without an additional high frequency modulation of the wavelength during the tuning in such a way that a monotonous wavelength time extent results without a high frequency modulation.

6. The method in accordance with claim 1, in which the tuning of the wavelength range in the positive direction is varied with a not necessarily constant velocity ≥0 and subsequently a change in the negative direction is varied with a not necessarily constant velocity ≥0, in this respect both directions or only one direction can be drawn on for the evaluation.

7. The method in accordance with claim 1, in which the artificial modulation is one of sinusoidal, rectangular or triangular.

8. The method in accordance with claim 1, in which the amplitude and/or the frequency of the artificial modulation is adapted for the evaluation in accordance with the wavelength modulation spectroscopy.

9. The method in accordance with claim 1, in which the phase of the artificial modulation is adapted in such a way that, on the evaluation in accordance with the wavelength modulation spectroscopy, no further phase shift or signal rotation has to be added in order to achieve an ideal result.

10. A spectrometer, comprising:
   a light source for the generation of a light beam with a wavelength variable in a wavelength range,
   a measurement volume in which the gas component to be determined is present and through which the light beam propagates;
   a controller for the light source for tuning the wavelength range without an additional high frequency modulation of the wavelength during the tuning in such a way that a monotonous wavelength time extent results without high frequency modulation;
   a light detector for detecting the intensity of the light beam after passage through the measurement volume;
   memory for the storage of measurement points that respectively consist of a point in time and an associated intensity value during the tuning, whereby a direct absorption line is obtained;
   an evaluation unit for generating an artificial measurement curve from the stored measurement points by shifting the measurement points on the axis of time, wherein the shift takes place such that following the shift an additional high frequency modulation results in the wavelength time extent, the evaluation unit further evaluating the artificial measurement curve in accordance with the methods of the wavelength modulation spectroscopy and determining a first concentration value therefrom.

11. The spectrometer in accordance with claim 10, wherein the evaluation unit is configured in such a way that the measurement points that respectively consist of a point in time and an associated intensity value can be evaluated in accordance with the method of direct absorption spectroscopy and in this way a second concentration value can be determined.

12. The spectrometer in accordance with claim 10, wherein the light source is a laser whose emission wavelength can be changed by a control current or a control voltage.

13. The spectrometer in accordance with claim 12, wherein the tuning takes place by a linear change of the control current or of the control voltage.

14. The spectrometer in accordance with claim 12, wherein the tuning takes place by a nonlinear change of the control current or of the control voltage.

15. The spectrometer in accordance with claim 10, wherein the tuning of the wavelength range in the positive direction is varied with a not necessarily constant velocity $\geq 0$ and subsequently a change in the negative direction is varied with a not necessarily constant velocity $\geq 0$, in this respect both directions or only one direction can be drawn on for the evaluation.

* * * * *